(12) United States Patent
Dimitrijevich

(10) Patent No.: US 6,599,526 B2
(45) Date of Patent: Jul. 29, 2003

(54) PERICARDIAL ANTI-ADHESION PATCH

(75) Inventor: Slobodan Dan Dimitrijevich, Bedford, TX (US)

(73) Assignee: The University of North Texas Health Science Center at Fort Worth, Fort Worth, TX (US)

(*) Notice: Subject to any disclaimer, the term of this patent is extended or adjusted under 35 U.S.C. 154(b) by 0 days.

(21) Appl. No.: 09/932,617

(22) Filed: Aug. 17, 2001

(65) Prior Publication Data

US 2002/0028233 A1 Mar. 7, 2002

Related U.S. Application Data

(60) Provisional application No. 60/226,503, filed on Aug. 18, 2000.

(51) Int. Cl.[7] .............................. A61K 9/70; A61F 2/02
(52) U.S. Cl. ....................... 424/448; 424/443; 424/444; 424/422; 424/423; 424/426
(58) Field of Search .................................. 435/243, 240, 435/241; 424/443, 464, 465, 427, 484, 471.4, 422, 423, 426; 604/891.1

(56) References Cited

U.S. PATENT DOCUMENTS

| | | | | |
|---|---|---|---|---|
| 4,703,108 A | * | 10/1987 | Silver et al. | 530/356 |
| 4,837,285 A | * | 6/1989 | Berg et al. | 530/356 |
| 5,223,420 A | | 6/1993 | Rabaud et al. | |
| 5,591,716 A | | 1/1997 | Siebert et al. | |
| 5,618,553 A | * | 4/1997 | Kelleher | 424/428 |
| 5,762,966 A | | 6/1998 | Knapp, Jr. et al. | |
| 5,770,209 A | * | 6/1998 | Grotendorst et al. | 424/198.1 |
| 6,086,863 A | | 7/2000 | Ritter et al. | |
| 6,087,552 A | | 7/2000 | Gregory | |

OTHER PUBLICATIONS

*Peritoneal Surgery*, Chapter 35, "Adhesion Prevention: Past the Future" by David M. Wiseman, pp. 401–417A, (1999).
*Archives of Othopaedic and Traumatic Surgery* 1987, "Decreased Adhesion Formation in Flexor Tendons by Topical Application of Enriched Collagen Solution—A Histological Study", Nyska et al., pp. 192–194.
*Vol. XXXIV Trans Am Soc Artif Intern Organs*, 1988, "A Biodegradable Antiadhesion Collagen Membrane with Slow Release Heparin", Miyata et al., pp. 687–691.
*Journal of Biomedical Materials Research*, vol. 24, 291–297 (1997), "In vivo evaluation of a collagenous membrane as an absorbable adhesion barrier", Edwards et al., pp. 291–296.
"8.2 Hazards and Prevention of Postsurgical Pericardial Adhesions" by David M. Wiseman, pp. 240 0 254, (1996).

* cited by examiner

*Primary Examiner*—Gollamudi S. Kishore
*Assistant Examiner*—Micah Paul Young
(74) *Attorney, Agent, or Firm*—Bracewell & Patterson LLP

(57) ABSTRACT

The present invention is directed to an anti-adhesion patch, which is constructed using a tissue equivalent technique. The anti-adhesion patch comprises a collagenous material and at least one non-living cellular component. Also provided is a method for preventing tissue adhesions between organs and other tissues being operated upon during surgical procedures by utilizing the anti-adhesion patch disclosed herein.

15 Claims, 14 Drawing Sheets

MINI-PATCHESS (HSDMEM):

| HRS. | AVERAGE | N | STANDARD DEVIATION | STANDARD ERROR |
|---|---|---|---|---|
| 0 | 100.000% | 12 | 0.000% | 0.000% |
| 24 | 100.000% | 12 | 0.000% | 0.000% |
| 48 | 96.740% | 12 | 5.107% | 1.474% |
| 72 | NA | | | |
| 96 | NA | | | |
| 120 | 90.218% | 12 | 3.763% | 1.086% |
| 144 | NA | | | |
| 168 | 88.768% | 12 | 2.235% | 0.645% |
| 192 | 84.058% | 12 | 5.664% | 1.635% |
| 216 | 80.435% | 12 | 6.272% | 1.811% |
| 240 | 73.553% | 12 | 9.536% | 2.753% |
| 264 | NA | | | |
| 288 | 67.391% | 12 | 8.987% | 2.594% |

MINI-PATCHES (HSF-12):

| HRS. | AVERAGE | N | STANDARD DEVIATION | STANDARD ERROR |
|---|---|---|---|---|
| 0 | 100.000% | 4 | 0.000% | 0.000% |
| 24 | 100.000% | 4 | 0.000% | 0.000% |
| 48 | 100.000% | 4 | 0.000% | 0.000% |
| 72 | NA | | | |
| 96 | NA | | | |
| 120 | 94.563% | 4 | 2.175% | 1.088% |
| 144 | NA | | | |
| 168 | 93.475% | 4 | 2.511% | 1.256% |
| 192 | 93.475% | 4 | 2.511% | 1.256% |
| 216 | 93.475% | 4 | 2.511% | 1.256% |
| 240 | 93.475% | 4 | 2.511% | 1.256% |
| 264 | NA | | | |
| 288 | 92.388% | 4 | 2.175% | 1.088% |

MINI-PATCHES (F-12):

| HRS. | AVERAGE | N | STANDARD DEVIATION | STANDARD ERROR |
|---|---|---|---|---|
| 0 | 100.000% | 12 | 0.000% | 0.000% |
| 24 | 100.000% | 12 | 0.000% | 0.000% |
| 48 | 100.000% | 12 | 0.000% | 0.000% |
| 72 | NA | | | |
| 96 | NA | | | |
| 120 | 99.638% | 12 | 1.256% | 0.363% |
| 144 | NA | | | |
| 168 | 99.638% | 12 | 1.256% | 0.363% |
| 192 | 99.638% | 12 | 1.256% | 0.363% |
| 216 | 99.638% | 12 | 1.256% | 0.363% |
| 240 | 99.638% | 12 | 1.256% | 0.363% |
| 264 | NA | | | |
| 288 | 99.638% | 12 | 1.256% | 0.363% |

FIG. 3A TABLE 1

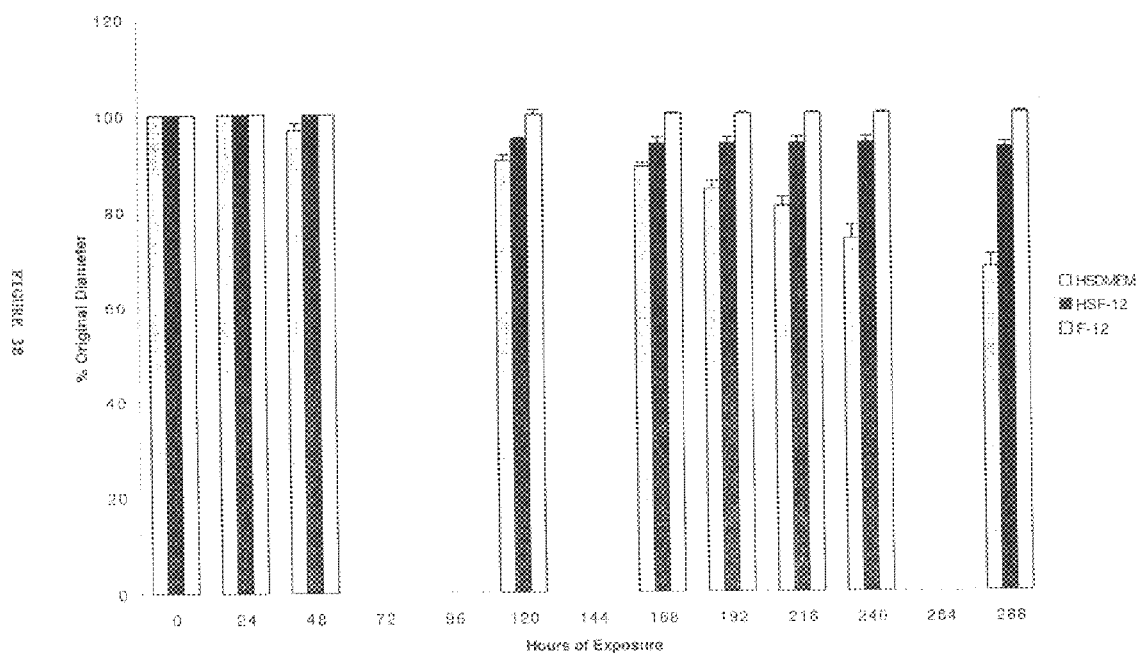

20ml- Full Size PAP ( HSDMEM)
| Hrs. | Average | Standard Deviation | Standard Error |
|---|---|---|---|
| 0 | 100.000% | ± 0.000% | ± 0.000% |
| 24 | 100.000% | ± 0.000% | ± 0.000% |
| 48 | 100.000% | ± 0.000% | ± 0.000% |
| 72 | 99.690% | ± 1.037% | ± 0.299% |
| 96 | 91.350% | ± 4.812% | ± 1.389% |
| 120 | NA | NA | |
| 144 | 83.330% | ± 7.693% | ± 2.221 |
| 168 | 61.770% | ± 9.177 | ± 2.649 |
FIG. 4A TABLE 2
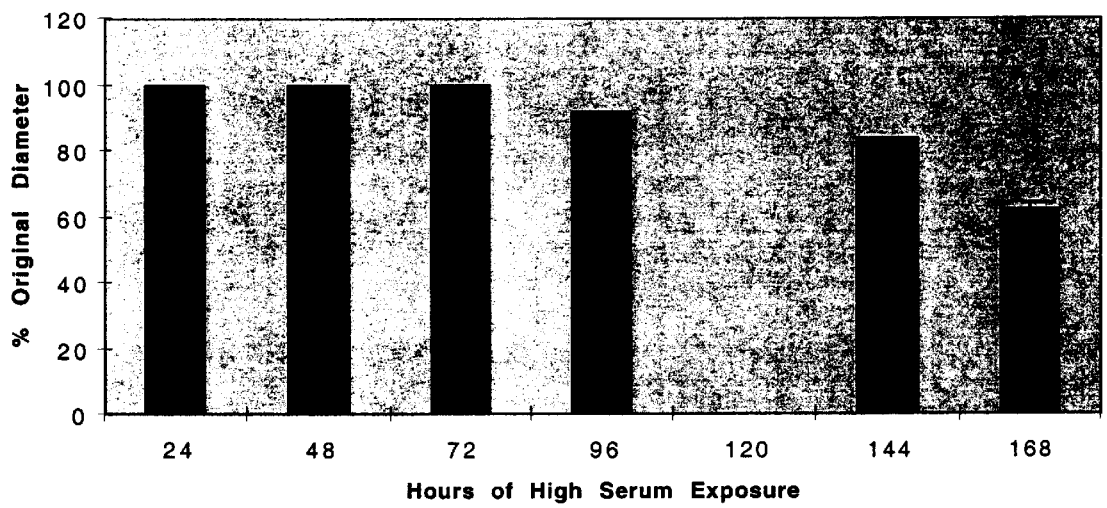
FIG. 4B. GRAPH 2

US 6,599,526 B2

PERICARDIAL ANTI-ADHESION PATCH

CROSS-REFERENCE TO RELATED APPLICATIONS

This invention claims the benefits of provisional patent application Ser. No. 60/226,503, filed Aug. 18, 2000.

FIELD OF THE INVENTION

The present invention generally relates to tissue equivalent technology. Particularly, the present invention relates to a pericardial anti-adhesion patch (PAP), a preformed loose collagenous acellular tissue, which comprises a collagen and at least one non-living cellular component that is reorganized prior to implantation into a patient. The patch prevents tissue adhesions between organs and other tissues being operated upon during surgical procedures and has to be maintained in place during the post-operative period when the mechanisms of adhesion formation are the most active (initial 2–3 weeks). Thereafter PAP diverts the wound healing process into the remodeling phase during which the anti-adhesion patch will be dissolved to component amino acids, predominantly prolyne and lysine.

DESCRIPTION OF THE PRIOR ART

Opening and entering of the body cavities is an intrusive event that exposes the surfaces of internal organs to a variety of traumatic conditions. The severity of trauma or injuries may range from desiccation and undue handling of the tissues, inadequate hemostasis, prolonged contact with foreign materials, misalignment of tissue planes in anastomosis, and failure to remove all abnormal tissues. During cardiothoracic surgery access to the coronary vasculature and the heart requires incision in the pericardial sack (i.e., pericardium) which envelops and isolates the heart from the chest walls and surrounding internal organs (e.g. lungs). Following such procedures, adhesions routinely form between the epicardium and the pericardium, sternum, pleura and other adjacent structures. Retrosternal adhesions cause injury to right ventricle, aorta, right atrium, innominate vein, and aortocoronary by-pass graft. In general, adhesion formation after cardiac surgery is associated with high morbidity and cannot usually be avoided. Once the surgery is complete, the chest cavity is closed but the incision (slit) in the pericardium may be loosely closed or left open. In either case due to post-surgical edema this incision usually becomes an oval opening. During the healing process the flaps of the pericardium adhere ("scar down") to the chest wall, the lungs and the heart itself. These adhesions occur in 100% of the cases and are a serious risk factor when there is a need for repeated surgeries. As repeated surgeries are now on the increase, there is a serious need for a method to prevent formation of pericardial adhesions in order to improve the success of the procedure. There are no devices approved by the FDA to prevent pericardial adhesions. Adhesions may also be ophthalmic, orthopedic, central nervous system, and intrauterine. It is therefore desirable to prevent post-operative adhesions not only in the thoracic cavity but also in all anatomical locations.

The surgical trauma involves tissue damage ranging from the incision itself to the loss of the measothelial cells that line the body cavity. Measothelial cells secrete fibrinolysin, an enzyme that dissolves fibrin. Inadequate hemostasis causes accumulation of blood and blood clots, and leads to formation and deposition of fibrin, which accumulates at the sites of injuries in the absence of measothelial cells. Fibrin is a very adhesive protein and glues injured surfaces together. Ischemia caused by surgery, although transient, allows the fibrin matrix to persist and gradually becomes populated by macrophages, fibroblasts, and giant cells. The initial adhesion matures as fibrin becomes fibrinous band with calcification nodules, and is often covered by measothelium which is formed after 4–5 days (complete in 10 days post-operatively). The adhesions can vascularize and even innervate, and in the last stages of maturation the adhesion becomes collagenized. This process involves activation of the principal connective tissue cells, which are involved in tissue repair, the fibroblasts, as well as the circulating immune system cells (macrophages). These cells begin to divide and migrate into the injured area as a part of a general inflammatory response. The fibroblasts secrete collagen (collagenization) and finally contract the collagen (fibrin) mass into a dense tissue. This contraction process further intensifies scar formation, forming stronger "adhesions" that "join" or "weld" the adjacent tissue surfaces, which were previously well separated. In time the adhesions become increasingly fibrous and may even calcify. Calcification is a highly undesirable aspect of adhesion formation. Some individuals (particularly of African American and Hispanic ethnicity) are genetically predisposed to severe scarring and therefore adhesion formation. These individuals are also at high-risk for cardiac problems which require surgical intervention. It is critical that the high-risk groups be protected from adhesion formation.

Prevention of adhesions has been a problem for a number of years and the most consistently applied strategy to prevent their formation has been to separate, physically, with "a barrier", the tissue surfaces which are likely to adhere. The anti-adhesion barriers were initially quite primitive (e.g. fine surgical steel wire mesh) and mostly biocompatible but non-biodegradable. In recent years, interest in more effective and biodegradable anti-adhesion barriers has intensified. However, a totally satisfactory solution is still to be found and development of new approaches is highly desirable. Particularly desirable are the strategies which may lead to a general solution to the problem of adhesion formation and which would prevent them in any anatomical location in the body. Advances in methodologies used for harvesting and culturing a wide variety of normal human cells and incorporation of these cells into three-dimensional matrices to form primitive tissue, now offer new opportunities for advances in adhesion prevention and design of a new generation of anti-adhesion barriers.

SUMMARY OF THE INVENTION

The present invention is directed to an anti-adhesion patch (Patch) and a method for constructing the Patch disclosed herein. Specifically, PAP is engineered tissue equivalent whose mechanical and optical properties arise from organization of collagen type I gel by human fibroblasts, but which in its final form is acellular. In detail, the Patch is constructed by mixing normal human connective tissue cells, preferably fibroblast, or vascular smooth muscle cells, and a collagen such as collagen type I solution. The resulting mixture is incubated to stimulate the cells to adapt to and organize the collagen gel matrix into a mono-cellular tissue equivalent (MCTE) having desirable dimensions and mechanical properties.

The present invention is further directed to a method of preventing tissue adhesions between organs and other tissues being operated upon during surgical procedures by utilizing the anti-adhesion patch disclosed herein.

Other and further aspects, features, and advantages of the present invention will be apparent from the following description of the presently preferred embodiments of the invention given for the purpose of disclosure.

BRIEF DESCRIPTION OF THE DRAWING

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2A shows a light microgram of the prototype Patch in which live cell are seen stretched and interacting with the matrix. FIG. 2B shows a light microgram of the prototype Patch after the cells have been killed and the debris and medium washed out. There are no neutral red positive cells.

FIG. 3A shows changes in the diameter but not the thickness of mini-patches which are used to develop matrix organization conditions. This experiment has been repeated several times and the results are statistically significant as indicated by very small error bars.

FIG. 3B is a bar graph demonstrating the results obtained during matrix reorganization experiments tabulated in FIG. 3A. It is noted that conditions of high serum (20% FBS in DMEM) produces the best results. High serum in Ham's F12 medium has a marginal effect which levels off whereas the negative control conditions (Ham's F12 with 5% FBS) maintain stable quiescent conditions. The significance of the latter is that patches may be produced and held in one organizational state and then induced to proceed in the desired direction by placing them in the 20% FBS in DMEM. The latter conditions are then used in the preparation of the PAP.

FIG. 4A tabulates the change in diameter of the full size prototype PAP when subjected to the conditions developed and shown in FIG. 3A above. FIG. 4B is the graphical representation of matrix reorganization for prototype PAP.

FIG. 8A shows that once the incision is made in the pericardium and the mammary artery severed and ligated, the Patch is brought over the pericardium and attached to the epicardium. The Patch is located under and over the anastomosis, and attached to the epicardium with Nitinol Couplers. FIG. 8B shows that before attachment, the Patch may be lifted or moved around on the beating heart to provide best possible protection. FIG. 8C shows that the pericardium is then closed with 2–3 sutures. FIG. 8D shows that the second patch is then placed over the closed pericardial incision and attached to the pericardium with Nitinol Couplers. FIG. 8E shows all the organs in place arranged before closure of the chest cavity.

FIG. 9A shows a total dissolution of the Patch placed over the closed incision in the pericardium. There are also no adhesions between the protected pericardium and the lungs. FIG. 9B shows that the pericardium has healed, closed and is loose. In this closed situation it is evident that there are no adhesions to the heart. This is confirmed by opening the pericardium. FIG. 9C shows it is easy to reopen the pericardium and observe the unobstructed anastomosis because the Patch has dissolved. FIG. 9D shows that LIMA can be lifted free of the epicardium easily and manipulated for a possible by-pass. FIG. 9E shows that there are no adhesions between the pericardium and the epicardium and the surgeon can completely grasp the heart and lift clear of the pericardial sack. Also all the coronary vessels are easily seen and are not obscured by adhesions, if necessary a coronary by-pass could be carried out.

DETAILED DESCRIPTION OF THE INVENTION

Figure 1A:
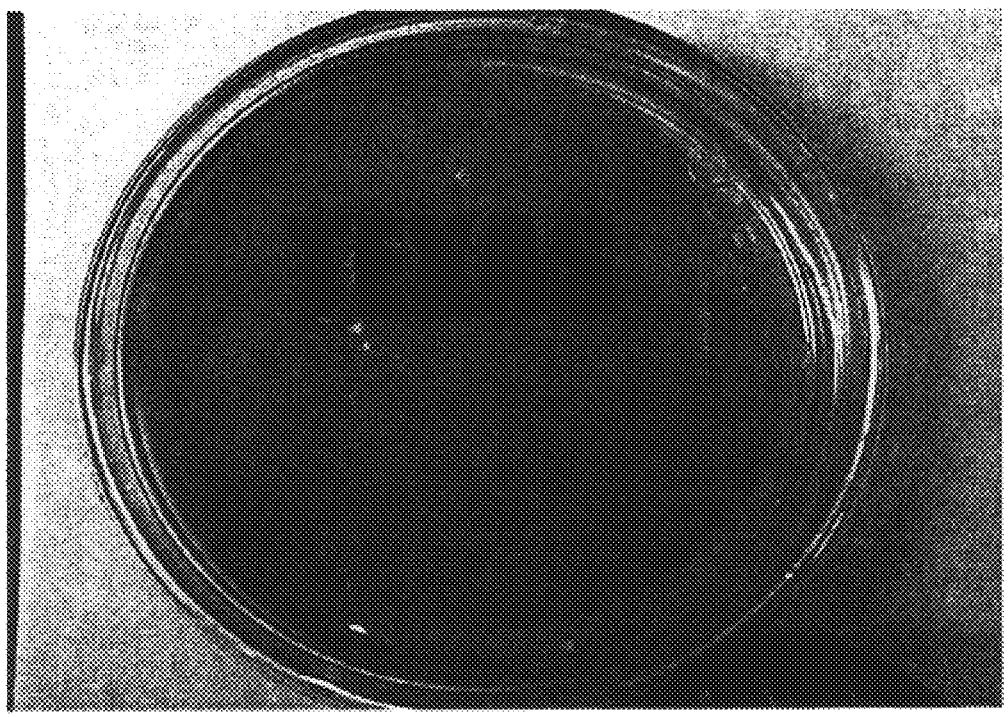
FIG. 1A shows the prototype Patch after initial adaptation of cells (fibroblasts) to the three-dimensional collagen type I environment. This is at a time point of 48 hrs after the start of the experiment (preferred time in the 24–96 hour window during which the medium is changed every 24 hours, preferably every 12 hours). The coloration of the Patch due to the diffusion of the medium into matrix is generated by a pH indicator present in the medium. It is noted that the Patch is quite translucent.

The present invention is directed to an anti-adhesion patch (Patch) and methods of utilizing the Patch for adhesion prevention.

In one embodiment of the present invention, there is provided an anti-adhesion patch comprising a collagenous material and at least one non-living cellular component. Preferably, the collagenous material is collagen type I or a combination of collagen type I and a co-component such as elastin, interstitial collagens, collagen type III, V and IX, glycoproteins and proteoglycans. The collagen can be from a natural source or a recombinant source (i.e., produced by an engineered cell line). Still preferably, the non-living cellular component is either from a natural source, such as human connective tissue cell or from a recombinant source. Examples of human connective tissue cells include fibroblast cells and vascular smooth muscle cells. More preferably, the fibroblast cell is a dermal fibroblast cell.

In another embodiment of the present invention, there is provided a method of constructing an anti-adhesion patch, comprising the steps of: (a) mixing human connective tissue cells with a collagenous material; (b) incubating the resulting mixture in a matrix organization medium to stimulate the cells to adapt to and organize the collagenous material into a mono-cellular tissue equivalent having desirable dimensions and mechanical properties; (c) treating the tissue equivalent to eliminate the cells; and (d) confirming the absence of viable cells in the tissue equivalent after the treatment. The resulting tissue equivalent may be used as an anti-adhesion patch. Preferably, the collagenous material is in an acid solution and first neutralized at 4° C. before the mixing step. An example of the acid is hydrochloric solution.

In a preferred embodiment, the human connective tissue cell is a fibroblast cell or a vascular smooth muscle cell. More preferably, the fibroblast cell is a dermal fibroblast cell.

In another preferred embodiment, the collagenous material is collagen type I or a combination of collagen type I and a co-component such as elastin, interstitial collagens, collagen type III, V and IX, glycoproteins and proteoglycans. The collagenous material is either from a natural source or a recombinant source.

In still another preferred embodiment, the acidic solution is hydrochloric solution, and the matrix organization medium either contains fetal bovine serum or is a serum-free cocktail of growth factors selected from the group consisting of fibroblast growth factor (FGF), epidermal growth factor (EGF), platelet derived growth factor (PDGF), transforming growth factor beta (TGF$_\beta$) and a mixture thereof in the presence of growth promoters, e.g., transferrin, insulin, etc.

In yet another preferred embodiment, the cell-elimination treatment includes nutrient deprivation, antibiotics treatment and treatment with anti-mitotics. Representative examples of antibiotics include puromycin, amphoteracin and mitomycin; and an example of anti-mitotics is 5-flurouracil.

In still another embodiment of the present invention, there is provided a method for preventing tissue adhesions between organs and other tissues being operated upon during surgical procedures, comprising the step of attaching an anti-adhesion patch to one of the surfaces of the tissues being operated upon. The anti-adhesion patch comprises a collagenous material and at least one non-living cellular component, and participates in formation of adhesion. Such anti-adhesion patch is biodegradable during the recovery. A representative example of the tissue operated upon is a heart. Preferably, the anti-adhesion patch is attached to the traumatized tissues using a tissue glue such as a fibrin tissue glue or another type of attachment (e.g. Nitinol Coupler).

In detail, one application of such Patch is described as follows. A special solution is used to kill the cells and wash out all the soluble biological material which might initiate an immuno-rejection and further enhance and prolong the inflammatory process. Initiation of immune reaction and undue inflammation is not desirable. It is envisaged that such a product, when kept sterile, refrigerated and moist, will have a favorable shelf life. By intervening between the incision in the pericardium and the heart, the Patch is made to be the target of the mechanism of adhesion formation at the critical time when the adhesion formation would normally take place. Upon dissolution of the patch, the critical phase of the tissue repair process during which the adhesions are formed has passed and the pericardium and the heart are well separated from each other. It is desirable after the closure of the chest cavity there is minimal inflammation as a result of implantation of the patch. This application would be most suitable for emergency surgical cases.

To apply the anti-adhesion Patch, an important component of the successful in vivo experiments is the method of attachment of PAP to the pericardium. Because suturing itself is an injury, a more appropriate way to address this issue is by using "fibrin glue" to glue PAP to the pericardium.

The following examples are given for the purpose of illustrating various embodiments of the invention and are not meant to limit the present invention in any fashion.

EXAMPLE 1

Engineered Tissue PAP

The patch tissue is constructed as a connective tissue equivalent using infant dermal fibroblast (or fibroblasts from other tissue) at a population density of approximately 350,000 cells/ml, and collagen type I at a concentration of approximately 4 mg/ml. The resulting mixture is then incubated. Only 2 concentrations of collagen I are commercially available, i.e., ~3 mg/ml and ~5 mg/ml. A mixture of these two solutions could provide an additional concentration of ~4 mg/ml. The collagen content controls the initial density and therefore mechanical properties of the construct. The size and shape of PAP is controlled by the size and shape of the casting container, whereas the thickness of the PAP depends on the quantity of collagen used. Initially PAP is cast in 100-mm tissue culture dishes. Once the PAP has adapted to the medium and the cells have adopted their normal morphology, the PAP is carefully detached from the tissue culture dish and the medium changed to DMEM containing 10–20% FBS but preferably 20% FBS for fast rate of organization. PAP may be allowed to organize to a size with desired mechanical properties. Alternatively, a proprietary coating process could be used to prevent the PAP from adhering to the petri dish without initiating contraction. It is projected that the contraction process may take several days. After the organization is complete, the medium is then aspirated and the PAP incubated in sterile phosphate buffered saline (PBS) until microscopic examination shows the absence of viable cells (this could be confirmed by neutral red staining of a piece of DE). The incubation continues with daily changes of PBS until all the biologically active molecules are removed from the matrix. The PAP is then incubated in sterile water at 4° C. to wash out all the PBS, after which it can be stored moist at 4° C. in a sterile ziplock bag until needed.

EXAMPLE 2

Sources of Cells

Normal human dermal fibroblasts may be purchased from Clonetics-Biowhitaker either as live cultures (in tissue culture flasks) or as ampoules of frozen stock cells stored under liquid nitrogen ($N_2$). The frozen cells are allowed to thaw until the ice pellet is free to move in the vial. The contents of the vial are pipeted into a 75 $cm^2$ vented cap tissue culture flask. To the flask is then added 15 ml Dulbeco's Modified Eagle Medium (DMEM) containing 10% FBS and the culture incubated at 37° and 5% $CO_2$ containing air. The medium is changed every second day until the cells populate about 80–90% of the growing. Fibroblasts are then further sub-cultured to expand numbers under the same conditions in DMEM containing 10% FBS. If the cells are purchased as cultures in 75 $cm^2$ tissue culture flasks, the flasks do not have vented caps and are completely filled with medium with no air space. The transport medium is removed and fresh growth medium (15 ml DMEM containing 15% FBS) added. After the culture has become 80–90% confluent the cells are using trypsin and sub-cultured as described in Example 3 below.

A problem with normal human cells is that they have a limited life span in vitro. It could be argued that cells from different donors have genetically dependent differences, although this is less evident when the source of tissue is infant foreskins. The ideal solution to this problem is to have a standard cell line which can deliver an endless supply of identical progeny. Unfortunately such cells are not normal and therefore are not acceptable in tissue engineering applications. In the future it is possible to utilize cell engineering techniques which would upregulate cell division without altering any other cell function. To date introduction of cDNA for catalytic subunit of human telomerase (hTERT) into cells comes close to achieving this. Hopefully, other methods, which do not involve alteration in hTERT activity, will become available.

EXAMPLE 3

Harvesting Cells for Xenograft PAP

Skin tissue remnants from circumcisions are obtained from the local newborn nursery or maternity ward (OBGYN). These are first decontaminated by soaking the remnants in serum free DMEM containing 20% penicillin/streptomycin at 4° C. The subcutaneous fat is then removed from the foreskin and the decontamination repeated using the same medium except the concentration of penicillin/streptomycin in DMEM is 10%. The skin sample is then incubated in dispase (10 unit/ml) for 48 hrs at 4° C. after which time the epidermis can easily be pulled from, detached and removed from the dermis. The dermis is rinsed several times in PBS and then cut a into very small pieces (2–3 $mm^2$) which were placed on to the inner surface of a 75 $cm^2$ vented cap tissue culture flask. The pieces were allowed to attach to the flask by incubating at 37° C. in an incubator (5% $CO_2$ and 98% humidity) for 10–20 min, after which time DMEM containing 10% FBS (10 ml) is added to the flask. It is critical that the dermal tissue pieces stay attached to the flask. After about 5–10 days of incubation and regularly careful changes of medium, the cells grow out from the explanted tissue and begin to populate the flask. At this point the tissue pieces are removed carefully and the culture continued, with regular changes of medium every two days, until the cell population in the flask is 90% confluent. The medium is then removed from the flask and the cells detached ("lifted") using trypsin/EDTA (5 ml). After treatment with trypsin inhibitor (2×the volume of trypsin/EDTA used) the cells are counted using hemacytometer, pelted by centrifugation, supernatant removed and the pellet re-suspended in fresh DMEM (with 10% FBS) and plated into several 150 cm tissue culture flasks (the split ratio depends on the original number of cells used and is usually between 1:4 and 1:8). Thereafter the cells may be expanded on the regular bases and surplus frozen and stored in liquid nitrogen. The required number may be used in the PAP construction.

EXAMPLE 4

Harvesting Cells for Allograft PAP

For this application the patient who decides on elective surgery has to donate a skin punch biopsy in order that his/her cells may be harvested and cultured to expand the cell numbers so that the cells could be incorporated into allograft PAP. The anatomical locations from which the punch biopsies are obtained are usually chosen to be sites that are not exposed and are esthetically acceptable to the patent. These are usually inside of the forearm or upper arm. The skin is cleaned, sterilized and local anesthetic administered. A full thickness 6-mm punch biopsy is then obtained and the wound closed with one or two stitches. The skin sample is kept sterile and is treated in the manner analogous to that described in Example 3 for the infant foreskin sample. Dermal fibroblasts are obtained in the identical fashion. When a sufficient cell number has been obtained, the PAP can be constructed and the preparation for surgery may begin.

EXAMPLE 5

Engineered PAP for Xenograft/Allograft

The PAP was prepared in exactly the same manner as described in Example 3 for the acellular PAP. The step initiating contraction of the tissue was omitted and the culturing continued using Ham's F12 medium as described in Example 3. After cultured for 5–10 days (but preferably 10 days), the PAP was ready for use. The steps in which the component cells were killed as outlined in Example 3 were also omitted.

The dermal fibroblasts, which contract and reorganize collagen matrix, are a specialized phenotype of these cells which are activated to participate in the wound healing process. Organization of the extracellular matrix, of which collagen type I is the major component, is a necessary phase of wound healing designed to close the wound. However, it is essential that this process be controlled and not excessive to form scar tissue which is too dense and therefore too difficult to vascularize and biodegrade. In order to accomplish this task, the fibroblasts change their phenotype to myofibroblasts which are characterized by expression of cytoskeletal proteins, such as alpha smooth muscle actin. In fact the myofibroblasts adopt the properties of their muscle tissue related cells, such as the smooth muscle cells, the physiological function of which requires them to contract and relax constantly. Another cell type which can and does contract collagen matrix is vascular smooth muscle cell, the major cellular component of the blood vessel walls. Therefore, these cells like the dermal fibroblast may be used beneficially in the construction of the PAP because they also will reorganize a collagen gel that they populate and improve the mechanical properties of the tissue that they are incorporated into. However, the mediators of vascular smooth muscle cell functions include substances with vasoconstrictive properties. Furthermore, the vascular smooth muscle cells can be used only in the acellular or xenographic versions of the PAP.

EXAMPLE 6

Harvesting of Vascular Smooth Muscle Cells

Human umbilical cord tissue was obtained from Caesarian Section births from donors who were free of human pathogens (hepatitis B/C, HSV, HIV, syphilis). The umbilical cord was cut into manageable lengths (preferably 10 cm) and the umbilical artery isolated by dissection from the surrounding connective tissue under sterile conditions. The artery lengths were tied at one end (sterile nylon thread), and filled, using blunt needle and syringe (10 ml), with Ham's F12 medium containing 20% penicillin/streptomycin, and then sealed off completely. After incubation at 4° C. in Ham's F12 containing 20% penicillin/streptomycin for 20 min, this decontamination process was repeated using Ham's F12 medium containing 10% penicillin/streptomycin inside and outside the artery pieces for 30 min. The arteries were then rinsed inside and outside with sterile PBS, filled with trypsin/EDTA (0.05%/53 mM, Gibco Life Technologies) and incubated under sterile conditions at 37° C. for 1 hour using the protocol described above. The solution containing endothelial cells was squeezed from the artery pieces and the process repeated with fresh solution of trypsin/EDTA three times. This protocol ensures that the vascular smooth muscle cells are not contaminated with the endothelial cells. For the fifth, sixth, and seventh washes using trypsin/EDTA, the incubation time is increased to 2 hours. These three washes were combined with the treatment of trypsin inhibitor and the umbilical artery smooth muscle cells (UASMC) isolated as pellet by centrifugation at 5,000 rpm for 3–5 min. The cells were re-suspended in SmGM2 defined medium (Clonetics-Biowhittaker), counted (hemacytometer), and plated into 25 $cm^2$ TC flasks. The cells were allowed to attach overnight and the unattached cells ("floaters") removed during the medium change 24 hours later. The cultures are allowed to grow to 80% confluence and subcultured at high seeding density, because these cells do not have a very high mitotic capacity and senesce after a few passages. A medium far superior to the commercially available formulations was developed for the culture of these cells.

EXAMPLE 7

Sources of Collagen

Collagen from several sources has been used for construction of tissue equivalents—the end result of tissue engineering. Rat tail collagen type I, extracted in house, was encountered in research applications, particularly in the early studies. Calf skin or bovine tendon are supplied as either a sterile viscous acidic solution (ICN Cellagen® 3% or 5%, pH 3.0) in acetic acid (Cohesion USA, Inc., Vitrogen® 3% in hydrochloric acid) or as a powder (Sigma). Collagen type I solution was also used from a European source (Cellon S. A., Brussels, Cellon®, a 3% solution in hydrochloric acid, pH 2.0). The disadvantage of using pre-made solutions of Collagen type I is that there is limited flexibility as to the collagen content of the Patch. The advantage is that since these are acidic, low pH excludes a wide range of microorganisms (particularly viruses). The use of an acidic solution is preferred because solubilization of collagen is difficult and sterilization of the resulting solution in the research laboratory setting is very time consuming and successful exclusion of microorganisms is uncertain.

A collagen type I solution for the PAP construction may be prepared by first mixing together thoroughly Cellagen AC3, Cellon, or Vitrogen (all containing 3 mg/ml of collagen type I), with Cellagen AC5 (containing 5 mg/ml of collagen type I in acetic acid with pH 3.0). The preferred ratio is a 1:1 mixture of AC3 and AC5 which provides a solution containing 4 mg/ml of collagen type I. To this solution (8 parts) was added Ham's F12 medium (10×, 1 part) and after thorough mixing, the mixture was neutralized at 4° C. (on ice) with reconstitution buffer (NaHCO3 NaOH, 1 part). The pH may further have to be adjusted to 7.4 when necessary by careful addition of 0.1M NaOH and kept at 4° C. until use. If the neutralized solution is allowed to warm up to room temperature, it will form into a gel, a one-way process which cannot be easily reversed without losses.

An issue often raised when collagen is considered in biomedical applications is the immunological reactions in humans to implanted collagen. Collagen is the most ubiquitous protein in the mammals with well-conserved amino acid sequence across species. Therefore in pure form it should evoke no immune response. Problems arise occasionally when methods of extraction and purification are inadequate. Thus immunologically active entities which are normally present in the source tissues remain trapped within the macromolecular structure of collagen and are then presented as antigens when introduced into the human body. Ideally the material that should be used is human recombinant collagen since there is very little point or chance of extracting human collagen from human tissue. However, as it may be concluded from earlier discussion on collagen synthesis, at cellular level this process is very complex and involves several intracellular and extracellular steps. So far the molecular biology approach of engineering a cell to produce collagen in a fashion that fermentation process can produce other recombinant proteins and peptides have not been successful. The recombinant product that has been disclosed by Fibrogen, Inc., (California) is not cross-linked and has to be remanufactured to approximate the extracted material. Its current price, even for research scale purposes is prohibitive, and the production capacity is impractical.

Alternatively, other macromolecules such as elastin, collagen type III, and glycosaminoglycans (GAGs) (e.g. keratan sulphate, chondroitin sulphate, etc.) may be also included in the matrix as co-components with collagen type I for constructing the Patch.

EXAMPLE 8

Organization of the Matrix in an Acellular Patch

Collagen deposition into the extracellular space is a complex process. It begins with the synthesis of soluble single chains which are post-translationally glycosylated and acted upon by prolyl hydroxylase which prepares prolyl residues for inter-chain cross linking and formation of triple helical soluble pro-collagen. The pro-collagen is extruded from the cell with leader peptides from which triple helical "rods" are cleaved and released. These rods can aggregated by longitudinal end to end association and also have their lysyl residues oxidized by extracellular lysyl oxidase in preparation for further lateral aggregation by cross linking. This process called fibrilogenesis, forms fibrils which are insoluble under physiological pH and temperature. It is the extracellular organization of collagen type I into fibrils and several sizes of fibers that confers mechanical integrity to the connective tissue. These collagen fibrils and fibers are insoluble and are deposited (precipitated) around the cells. There are certain known stimulators of collagen synthesis, the usual ones being oxygen, ascorbic acid (vitamin C) and glycolic acid. When these are added to the culture medium, they stimulate collagen synthesis. Ascorbate is incorporated into the medium used for the culture of the Patch. It is expected that culturing the Patch in the high serum conditions stimulates production and activity of lysyl oxidase.

Alternatively, mechanical integrity of the Patch may be also generated in the absence of cells by addition of specific (lysyl oxidase activity) or non-specific (horse radish peroxidase, HRP) oxidizing enzymes or any other cross linking agent or method that can initiate cross-linking of collagen and improve the mechanical properties of the PAP constructed in this fashion.

EXAMPLE 9

Mechanism of Matrix Organization of the PAP by Fibroblasts

Using cell surface receptors for the extracellular matrix (ECM) called integrins fibroblast can attach to specific regions (e.g. amino acid sequences RGD) of collagen and thus further organize the ECM. Fibroblasts regulate collagen concentration through synthesis and degradation. In the face of collagen deficiency (e.g. after injury) fibroblasts synthesize collagen. When collagen is over produced (fibrosis) fibroblasts degrade it by synthesizing and secreting collagenases. Although this regulatory process operates at low level as a normal part of tissue homeostasis (tissue maintenance is particularly elevated during wound healing/tissue repair and is principle mechanism of resolution of scars (tissue remodeling). Tissue remodeling is the basis for the biodegradation of the Patch.

Therefore, when fibroblasts are incorporated into collagen type I matrix, as is the case in the construction of the Patch, the initial culture period encourages the attachment (via integrins) of fibroblasts to collagen provided in the process. During the second phase of matrix organization, the fibroblasts are stimulated to: a) synthesize new collagen and excrete it into the extracellular space; b) by secreting lysyl oxidase further cause aggregation (fibril formation) and organization of newly synthesized collagen; and c) act in the same fashion to organize the collagen provided in the process. Fibroblasts also randomly move and redistribute themselves through the matrix attaching and mechanically pulling on the collagen in the process, and producing the integrity of the Patch. The culture process which is used to produce the Patch is therefore of multiphasic benefit.

The process of matrix organization is similar to formation and remodeling of provisional matrix during wound healing/ tissue repair. A major source of necessary ligands (e.g. growth factors and chemokines) that control the appropriate signal transduction pathways is serum. However, since serum composition with respect to these component is variable, bovine serum may not be desirable material to use under some circumstances. Then the serum free defined medium may be necessary. These usually substitute a cocktail of growth factors such fibroblast growth factor (basic or 2) (FGF2), epidermal growth factor (EGF), platelet derived growth factor (PDGF) and transforming growth factor beta ($TGF_\beta$) and in the presence of the usual compliment of growth promoters transferrin, insulin etc. These growth factors are now produced from human cDNA sequences using recombinant technology. The serum free medium can be used in the monolayer of cultures when the cells are expanded in number or when they are cultured within the collagen matrix. All methods of cell growth and maintenance need to be protected both as monolayers and when they are introduced into the collagen matrix and become three-dimensional culture.

EXAMPLE 10

Construction of the Patch

There are several variables during the construction of the Patch. First, collagen concentration can be 3, 4 or 5 mg/ml due to commercial availability. The higher the collagen concentration, the better the mechanical properties of the "Patch", i.e., some strength is derived from an increase in density of the tissue. However, the denser the tissue, the more it resembles a scar and the longer it takes to disintegrate and bio-adsorb.

The second variable that can be controlled is the cell number inoculated into the collagenous matrix. Since cells organize the collagenous matrix, the higher the number of cells, the better and more quickly the matrix is organized. The maximum cell number employed to date is 500,000 cells/ml of the collagen solution. This is the cell density to be used in the Patch construction.

The third variable is the time in culture of the Patch under non-contractile conditions. The longer the Patch is in the culture, the stronger it becomes due to an extended organization of the collagenous matrix by the component cells (fibroblasts).

And the fourth variable is the culture under matrix organization conditions. Several specific initiators of this process (e.g. thrombin, high calcium, $TGF_\beta$) may be used to control the matrix condensation process. Alternatively, combination between the collagen solution and a man-made biocompatible (and biodegradable) polymer may be used for this purpose, provided the criteria for the properties of the Patch are not compromised.

To construct the Patch, normal dermal fibroblasts were obtained by outgrowth of cells from de-epidermalized infant foreskin explants. Cells in early passage were harvested by trypsinization and used for construction of three-dimensional matrices (connective tissue equivalent). Fibroblasts (preferably, 300–360,000 cells/ml) were added and thoroughly dispersed into a cold (4° C.), neutralized (pH 7.4) collagen type I solution (20 ml, 3.0 mg/ml). Aliquots of the resulting mixture were poured into a 100 mm tissue culture dish and allowed to gel by incubation at 37° C., 5% $CO_2$. After equilibration period of 5–12 hrs, the cultures were treated with 20 ml medium of Ham's F-12 containing 5% FBS, ascorbate and α-ketoglutarate (or glycolic acid, or other collagen synthesis stimulators) and the medium (Ham's F12 containing 5%, or any defined media such as Clonetics FGM, Cascade Biologicals FGM, etc, which will support adaptation of FBS) changed thereafter every 48 hours for 1 week. At the end of this period the Patch was epartated from the walls and the floor of the dish using a flat spatula.

EXAMPLE 11

Matrix Reorganization in the Patch

By changing the medium to DMEM (containing up to 20% FBS, or using any other at defined media which contains $TGF_\beta$, lysophosphatidic acid (LPA), PDGF, thrombin, high calcium etc.), the cells were induced to reorganize the collagen gel into a tissue like matrix in a time dependent manner, while retaining a degree of translucency which allows visibility of vascular structures when located on the heart. This process of controlled tissue organization was continued by changing medium every 2 days and monitoring the patch diameter and thickness daily (see FIGS. 3A and 4A). After approximately 10 days in culture, the mechanical properties of the matrix were deemed appropriate and the Patch would have still retained substantial translucency.

In addition to improve the mechanical properties that contribute to ease of handling and attachment, it is also desirable to maintain the translucence of the Patch. This is because the surgeon has to be able to easily discern the vascular structures that are being covered by the Patch. This would be critical if there would be a need to reopen before the Patch has been adsorbed and a need to work on the cardiac vessels. The surgeon would just cut through the Patch to gain access to the vessels under it. Further advances in the mechanical integrity (ability to be sutured) may be made by incorporating other ECM macromolecules into the second and third generation Patches.

EXAMPLE 12

Elimination of Cellular Components from the Patch

When the Patch had reached about 60% of its initial size while retaining its thickness, the medium was removed, the PBS (1×, 20 ml) added, and the Patch was subsequently maintained at 4° C. The PBS was changed every 2–3 days for 1–2 weeks, the PBS was then removed and sterile water added (20 ml). After several changes of sterile water, the Patch was maintained moist at 4° C. until use. All operations were carried out under sterile conditions using sterile reagents. The absence of cellular component was confirmed with neutral red labeling for viable cells and light microscopy.

Other methods can be used to kill the cells. These include levels of common antibiotics (e.g. puromycin, amphoteracin, mitomycin etc.) which are toxic to mammalian cells as well as micro-organisms, or anti-mitotics such as 5-flurouracil (which are the older generation anticancer agents), and osmotic changes (high to low osmolar solutions). The nutrient deprivation is preferred because of ease of use. Whatever the method is, there is washout period first for the medium and then for cell killing solution.

In the case of elective surgeries, the Patch can be constructed and organized using patient's own cells. These fibroblasts could be obtained very simply from a 6 mm dermal punch biopsy and expanded to a number sufficient for several patches. One Patch currently uses approximately 7 million cells (one confluent 150 $cm^2$ TC flask). An approach that may but has not yet been formulated is to culture and bank tissues and cells for individuals in case they need them in the future.

The patch can certainly also be used to deliver mesothelial cells to the area where they have been eliminated as a result of surgical trauma. One possibility is human amniotic membrane. However, this material is not very desirable because it greatly increases the risks of contamination with human pathogens.

EXAMPLE 13

Inplantation of the Patch

Efficacy of PAP was evaluated in the canine model of "beating heart surgery" (adult mongrel dogs weighing 20–25 kg) using the experimental protocol approved by Institutional Animal Use and Protection Committee (IAUPC). In the first series of experiments the Patch was attached to the epicardium using Fibrin Sealant (Haemacure Corp., Sarasota, Fla.) after left thoractomy and the pericardium was left open. In the second series of experiments mammary artery anastomosis was performed and two PAPs were used: one was attached to the epicardium and the other to the closed pericardium. The attachment was carried out using Nitinol Coupler (Coalescent Surgical, Inc., Sunnyvale, Calif.).

EXAMPLE 14

Surgical Methodology

Experiments using the canine model were conducted in accordance with the Guide to the Care and Use of Laboratory Animals (NIH85-23, revised 1996) and with approval by IAUPC of the University of North Texas Health Science Center at Fort Worth. In each experiment, a mongrel dog (20–25 kg, male or female) was anesthetized using pentobarbital sodium (30 mg/kg body weight). Supplemental pentobarbital sodium and fentanyl (10 $\mu$g/kg body weight) were i.v. administered as needed to maintain a surgical plane of anesthesia. The dogs were intubated by tracheotomy and ventilated with room air by a Harward respirator. Arterial blood was frequently sampled and analyzed for $Po_2$, $Pco_2$, and pH; ventilation was adjusted to maintain these variables within limits of 100–140 mmHg, 35–45 mmHg, and 7.35–7.45 respectively. Sodium bicarbonate was administered i.v. to maintain normal arterial pH when $Pco_2$ was within the normal limits. Body temperature was measured with a rectal thermometer and was maintained at 36–37° C. by water circulating heating pad.

The myocardium was exposed via left thoracotomy in the fifth intercostal space. Incision was made in the pericardium and a portion of the inner surface of the pericardium and the epicardium (surface of the heart) were abraded with gause, and the anti-adhesion patch was placed over the epicardium to cover the incision. To keep it in place, the Patch was glued at the edges using fibrin "tissue glue" (Fibrin Sealant, Haemacure Corp., Sarasota, Fla.). The animal was then closed, brought out of anesthesia and returned to the recovery room and the chest tubes were removed. The duration of surgery was 2.5–3.0 hrs. The dog was monitored for rejection (temperature, lymphocyte count in the blood) to ensure that there were no massive inflammatory or rejection responses. Dogs did not require medication during their recovery or thereafter.

After a specific period of time (up to 6 months) the dog prepared as described above was anesthetized and left thoracotomy performed in the fifth intercostal space. The adhesion absence or presence in the control areas was evaluated and recorded photographically.

Another surgical procedure was also performed in dogs to mimic coronary artery bypass grafting. After anesthesia and left thoracotomy as described above left internal mammary artery (LIMA) was isolated in the area of the thoracic cavity in which it is unattached. A section 10–15 mm of LIMA was ligated off and removed to be used as mimic "graft" later in the experiment.

A pericardial "well" was created with an opening over the proximal Lateral Anterior Descending Coronary Artery (LAD), and a small area (3–5 mm long) of LAD was exposed by abrasion immediately over the artery. The LIMA graft was then sutured (using 6.0 proline suture) over the abraded LAD to mimic LIMA-LAD anastomosis. The other end of the LIMA graft was taken out through the pericardium and fixed thus leaving this end of the LIMA graft free (unattached) and located outside the pericardium. A 1–2 cm cut was made in the Patch and the Patch was placed on the heart in such a way that the cut accommodated the anastomosis. Also one part of the Patch was under the LIMA and the other covering it. The Patch could be attached to the epicardium with fibrin tissue glue, sutured and glued, or held in place using Nitinol Couplers (Coalescent Surgical, Inc., Sunnyvale, Calif.). The use of Nitinol Couplers is preferred. The pericardial "well" edges were approximated with three sutures leaving an opening of 3–4 mm. The second Patch was then placed on top of the pericardial opening and also secured to the pericardium using Nitinol couplers. The dog was then closed up and after recovery released from the post-operative recovery.

EXAMPLE 15

Termination of Experiments

In order to observe the efficacy of the Patch in preventing the formation of pericardial adhesions and also its dissolution time, the experimental dogs were subjected to the identical preparation procedure, anesthesia and opening of the thoracic cavity. The areas traumatized during the initial surgery were examined for formation of adhesions which were scored according to Adhesion Scoring Group (Fertility and Sterility, 1994; 62: 984). The lowest category is no adhesions, the next is the presence of filmy adhesions that may be resolved by passing a gloved finger between the adherent surfaces; and the worst class are those that required resolution using sharp instruments (scalpel). These observations were recorded photographically (digital camera). The animals were then euthenized according to the prescribed protocols.

EXAMPLE 16

Patch Construction Experiments

Figure 1B:
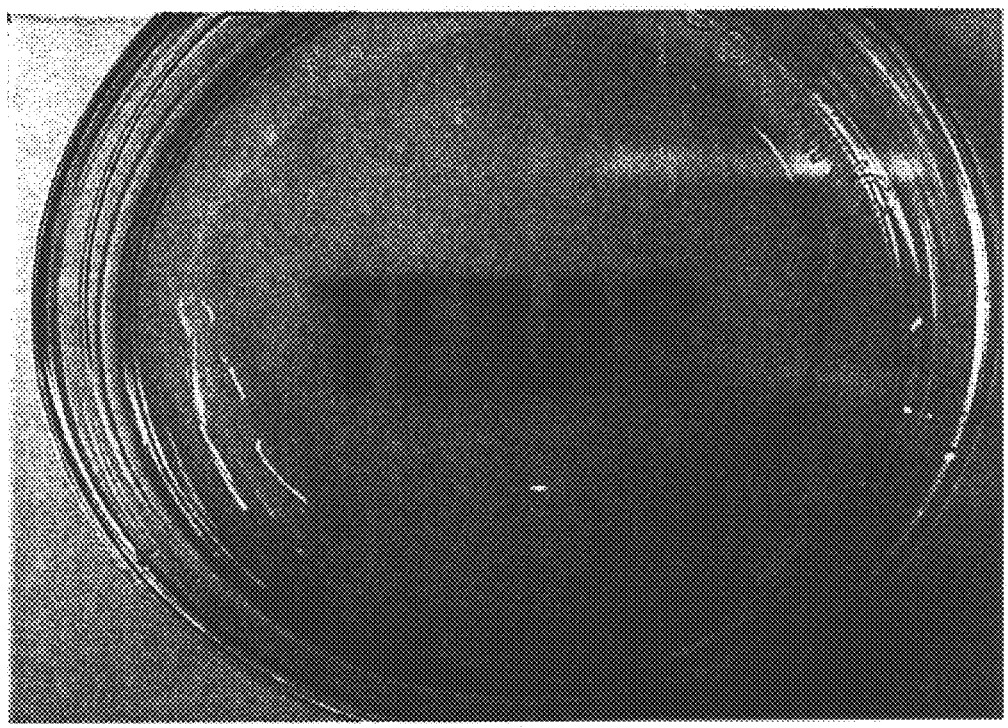
FIG. 1B shows the prototype Patch after the matrix reorganization process lasting 12 days, and incubation in phosphate buffered saline (PBS, pH 7.4) at 4° C. During the incubation, PBS is changed every 12 hours for 2–3 days. This process kills the cells and washes out all soluble cell debris and factors associated with the culture medium. An approximate indicator that this process is complete is that the prototype Patch loses the pink color and is now colorless. It is noted that the Patch is still substantially translucent.
Figure 2A:
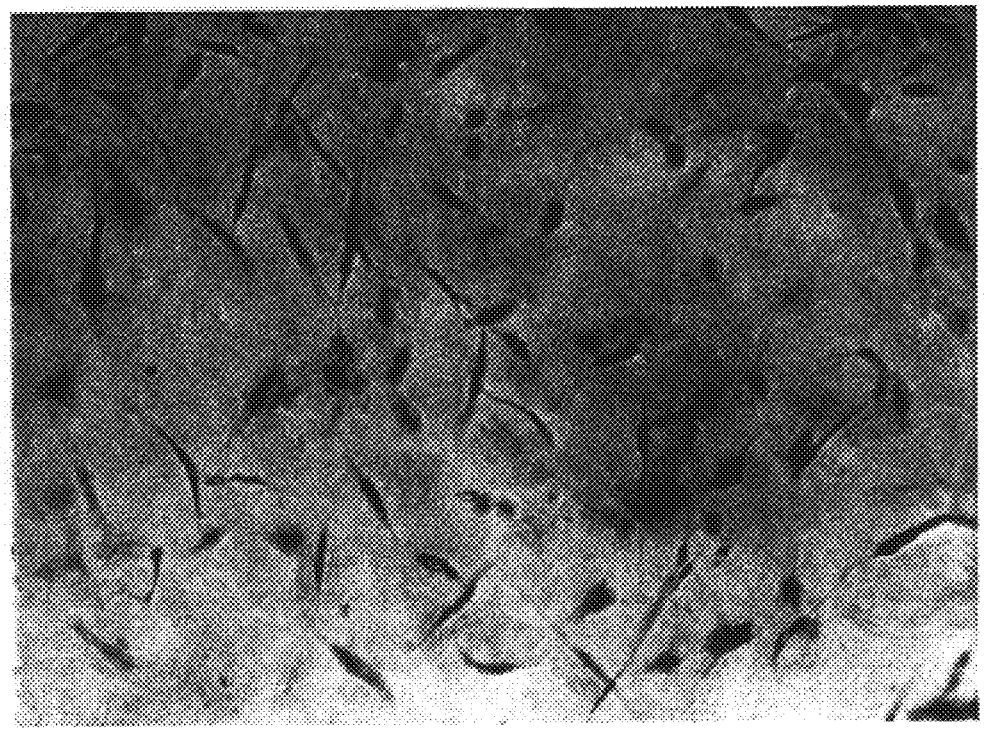
FIGS. 2A and 2B show that to confirm cell death, the Patch is labeled with neutral red and observed under light microscopy. Neutral red is a cell permeable indicator that react to the intracellular pH in the live cells with active metabolism, and a frequently used simple cell viability dye.
Figure 2B:
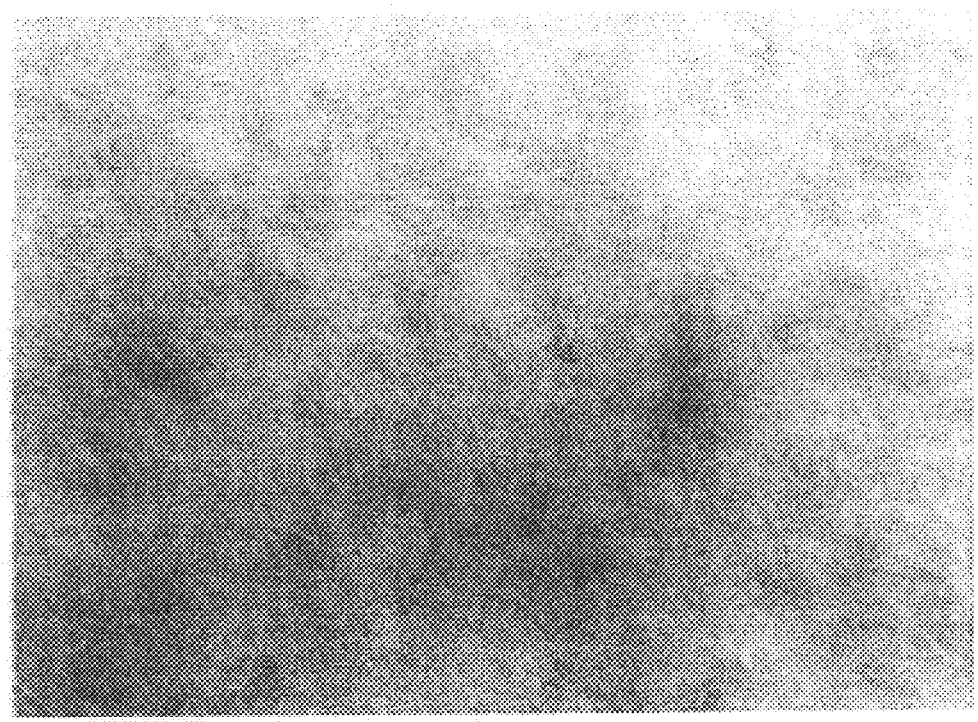
Figure 5A:
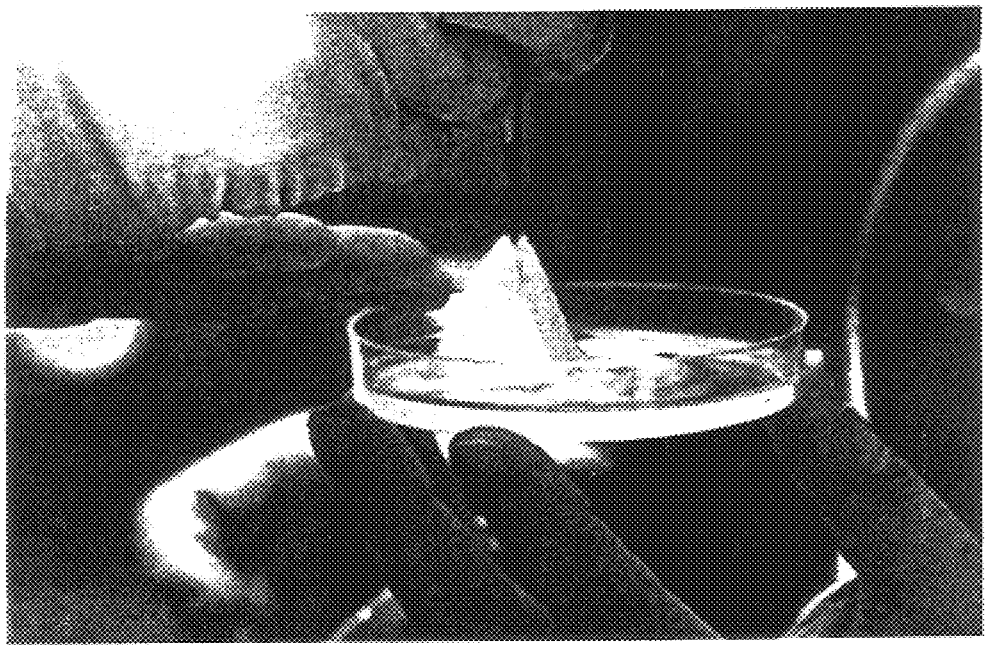
FIGS. 5A and 5B show preparation of the Patch before surgery. The Patch is clearly very easy to handle with surgical instruments (FIG. 5A). The Patch can also be cut and manipulated for precise localization on to the epicardium of the beating heart. It may also be picked up and moved around from one location to another (FIG. 5B).
Figure 5B:
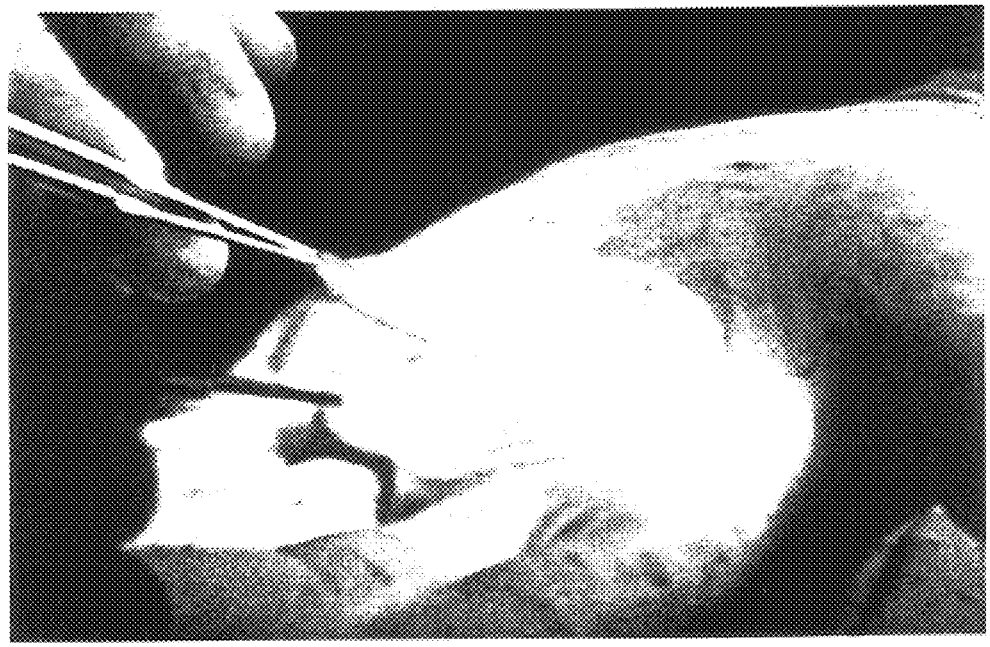
Figure 6A:
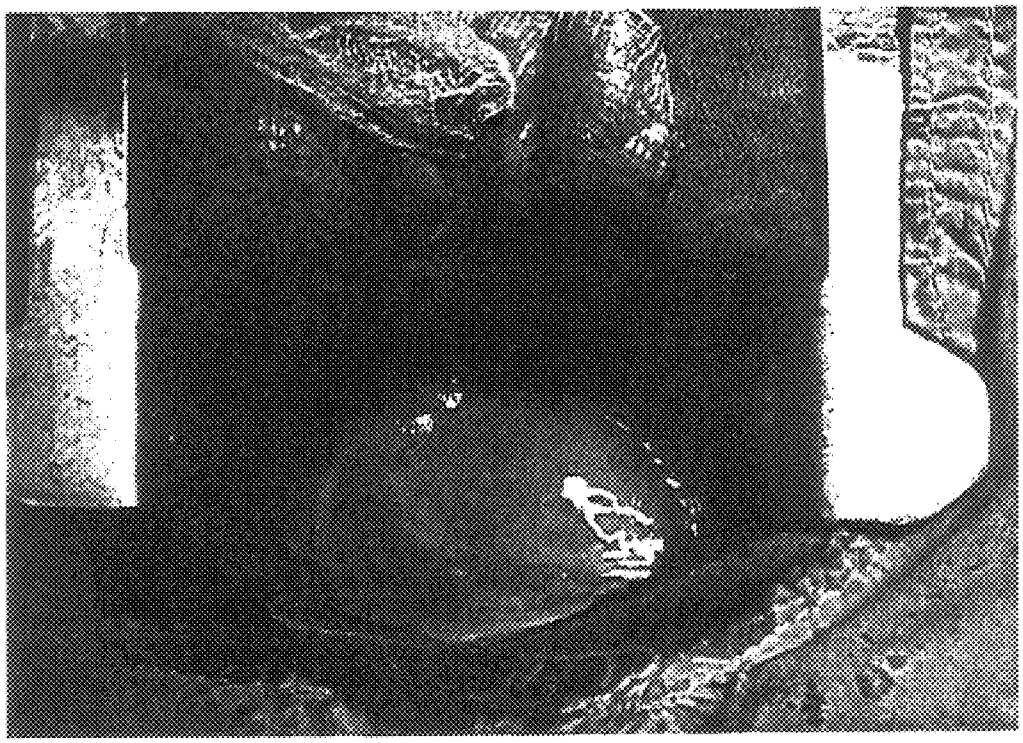
FIGS. 6A and 6B show the PAP on the epicardium after it has been attached to the pericardium using tissue sealant. In first series of experimental procedures the pericardium was left open (FIG. 6A). It is noted that although the Patch is not as translucent, the coronary vasculature is still clearly visible (FIG. 6B).
Figure 6B:
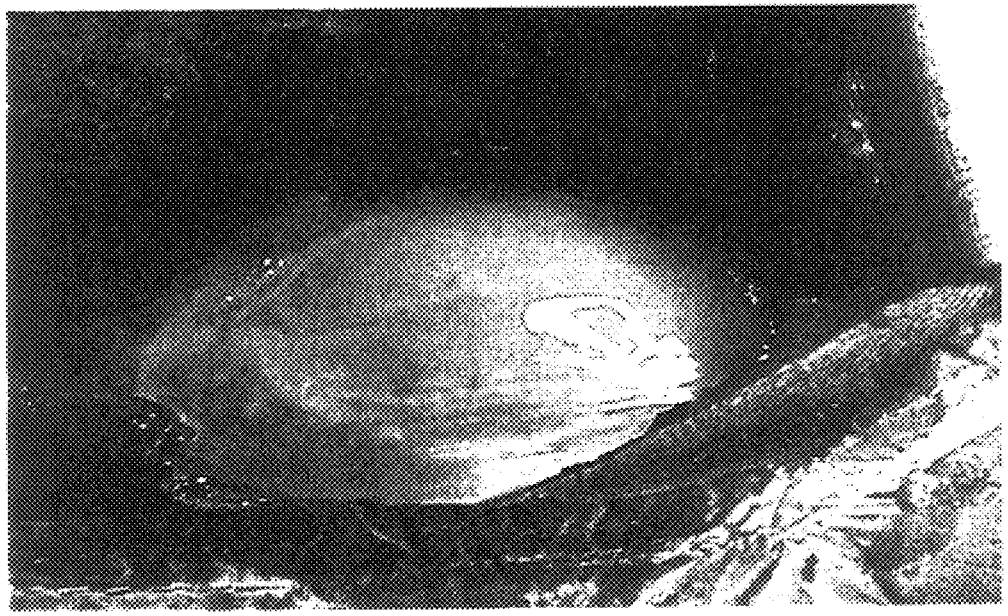

After preliminary experiments the Patches were constructed using the methodology described in Example 14 in batches of 12. FIGS. 1A and 1B show the statistical uniformity of the organization of the matrix by the cells. FIGS. 2A and 2B show the comparison of the tissue sections of the Patch before and after cell killing once the matrix has been organized. The cells in these figures were stained with hematoxolyn and eosin. Neutral red staining, which is an intracellular pH indicator, was also used to show whether the cells are alive or dead. FIGS. 3A and 4A show changes in the diameter but not the thickness of mini-patches which are used to develop matrix organization conditions. This concept is further demonstrated as a bar graph in FIGS. 3B and 4B. During the washout periods, using sterile PBS to remove the remnants of killed cells and the medium, and afterwards using sterile water to remove PBS are simple steps in the process but can potentially be sources of contamination if sterile solutions and strict sterile techniques are not used. Also care has to be taken not to disrupt the mechanical integrity of the Patch when the liquid is being aspirated. The Patch should be easy to handle and translucent enough to allow visibility of coronary vasculature (see FIGS. 5A, 5B, 6A and 6B).

EXAMPLE 17

Anti-Adhesion Experiments

Since the epicardium is not coated with a layer of mesothelial cells, in all experiments the Patch adhered to the epicardium whether it was abraded to stimulate adhesion formation or not. Therefore all other surfaces in the thoracic cavity are, when traumatized, the principal initiators of adhesion formation.

The above was demonstrated in the first series of experiments utilizing 3 dogs in which the pericardium was left open. This series also established that the dissolution time of the Patch was greater than 3 months. Experiments terminated at 2 and 3 months still showed a milky white membrane on the pericardium located at the Patch placement site. It was also evident that the Patch was a target for angeogenesis (vascularization) since microvasculature was evident from 2 months. This was considered to be beneficial since vascular system would contribute to resolution of the Patch by bringing macrophages and lymphocytes to the implantation site.

Figure 7A:
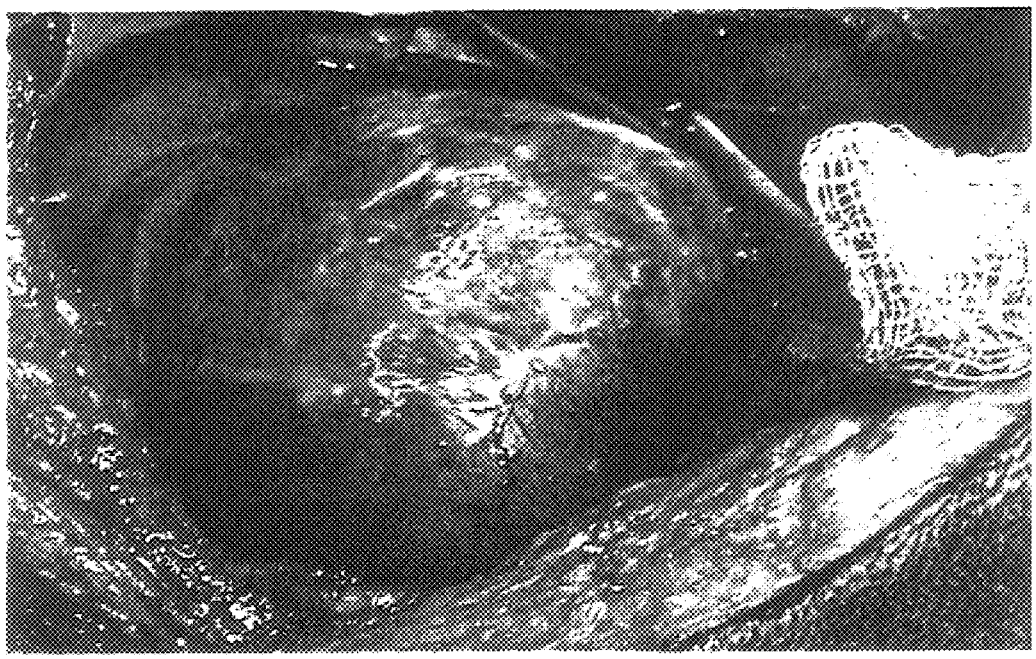
FIG. 7A shows that after the experiment has been terminated (4–5 months postoperatively), the Patch is totally dissolved.
Figure 7B:
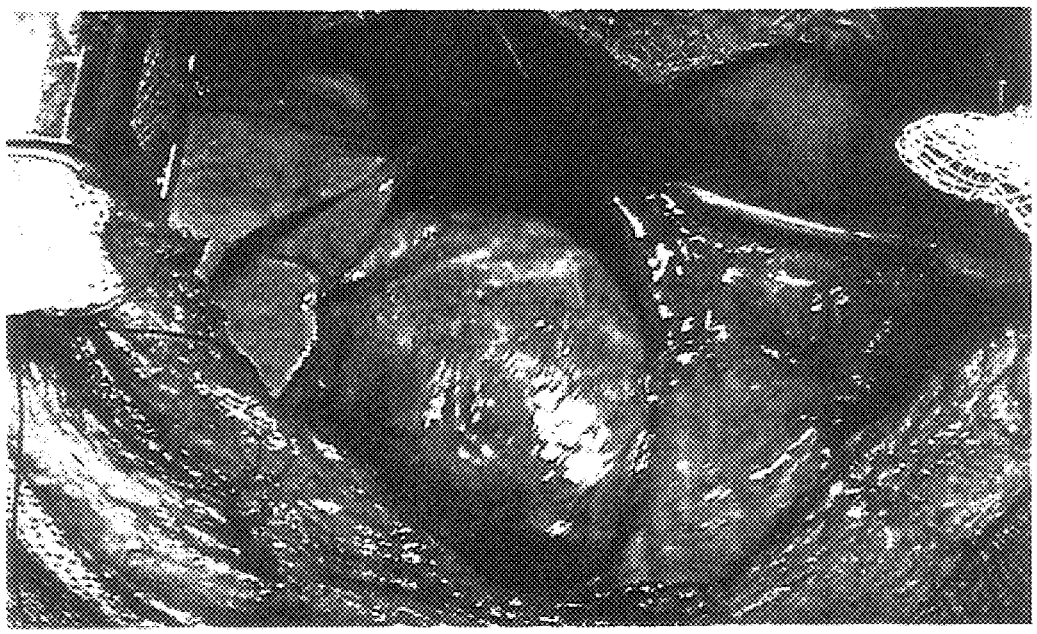
FIG. 7B shows that there are no adhesions between the lungs and the pericardium, lungs and the heart and the pericardium and the heart in the locations that are protected by the Patch.
Figure 7C:
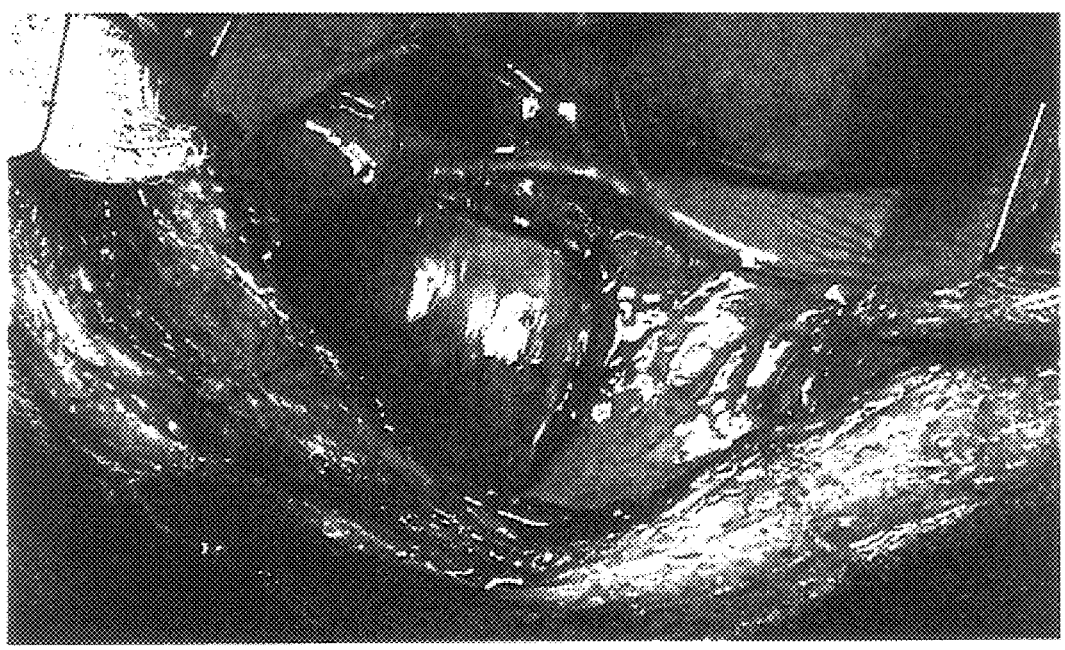
FIG. 7C shows that in the area unprotected by the Patch, weak adhesion formations occur (grade 0.5–1, resolvable with gloved finger).
Figure 7D:
FIG. 7D shows that some of the adhesions in the unprotected area can be quite substantial (grade 3, resolvable with sharp surgical instrument).
Figure 8A:
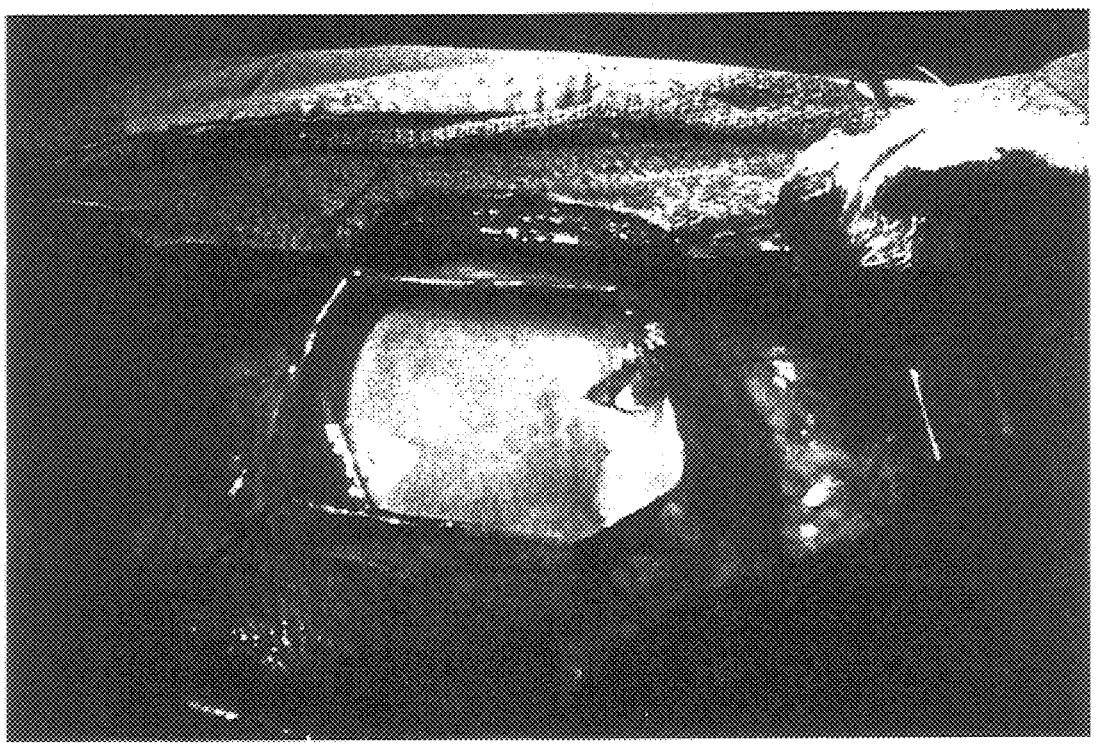
FIGS. 8A–8E show application of the Patch for the LIMA procedure.
Figure 8B:
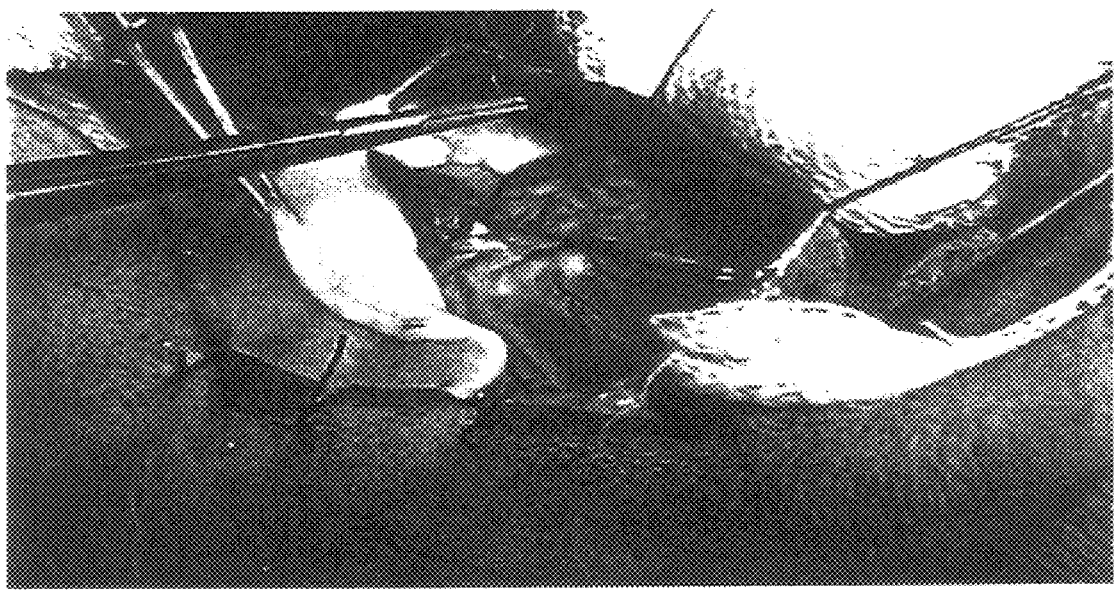
Figure 8C:
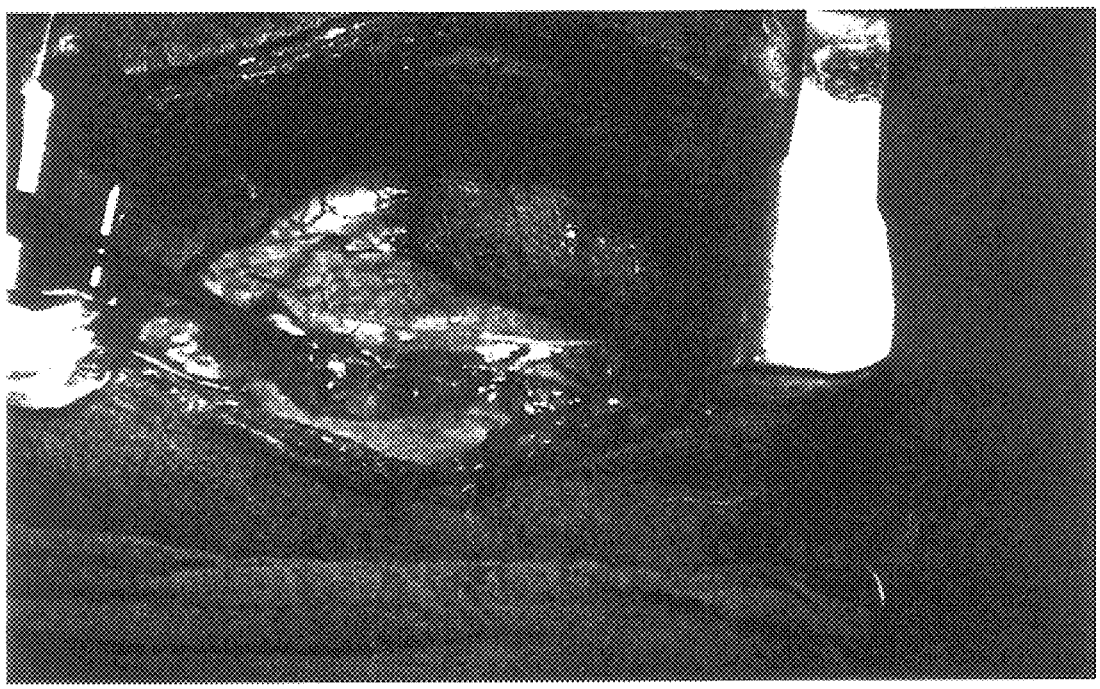
Figure 8D:
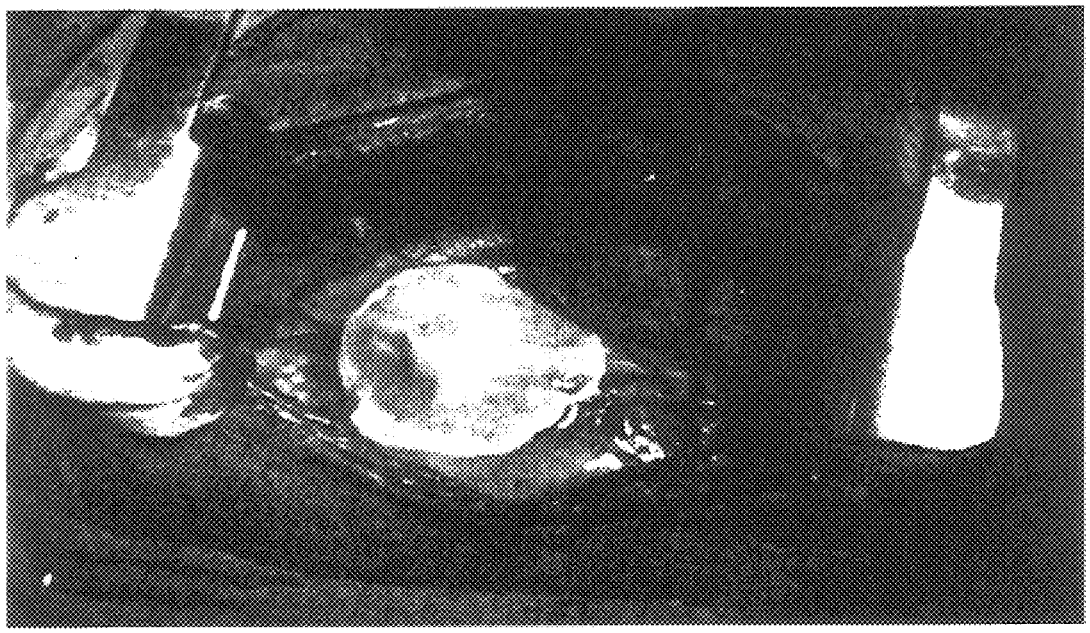
Figure 8E:
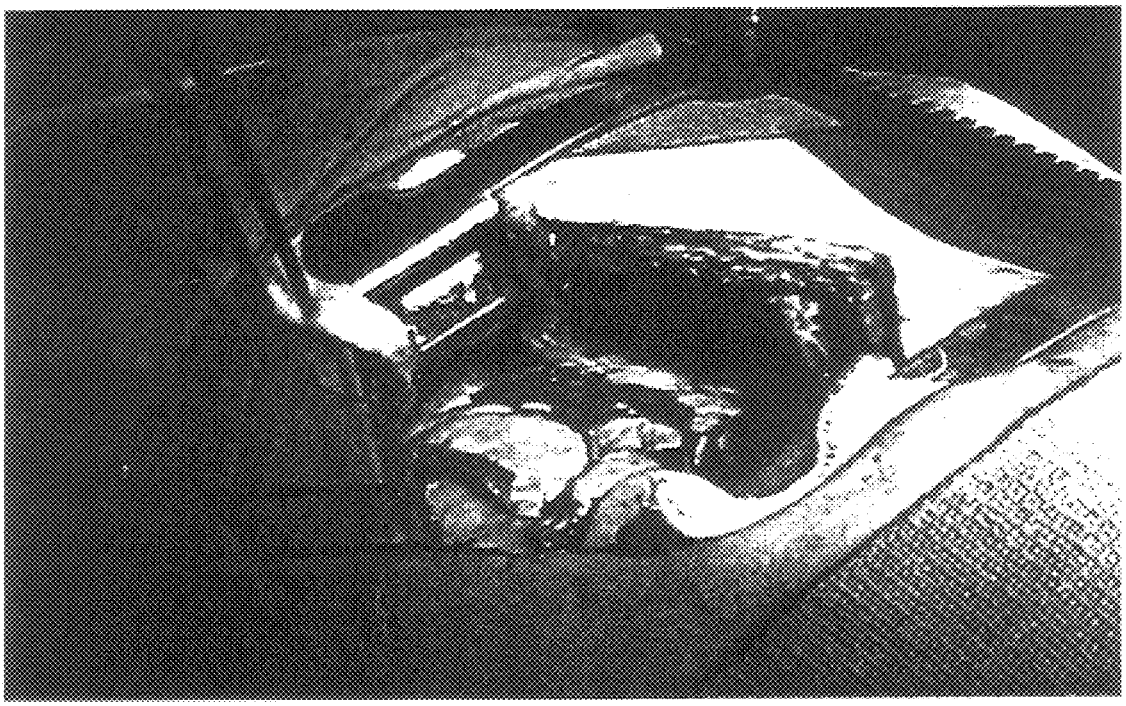
Figure 9A:
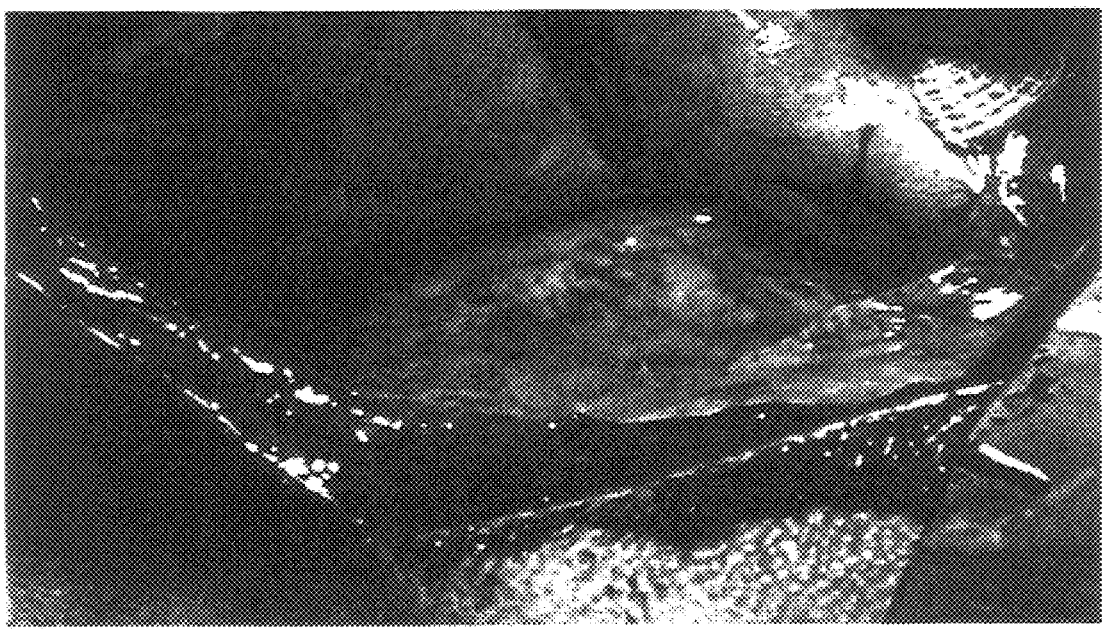
FIGS. 9A–9E show the results obtained on re-opening the animals 4 months after the LIMA experiment has been performed.
Figure 9B:
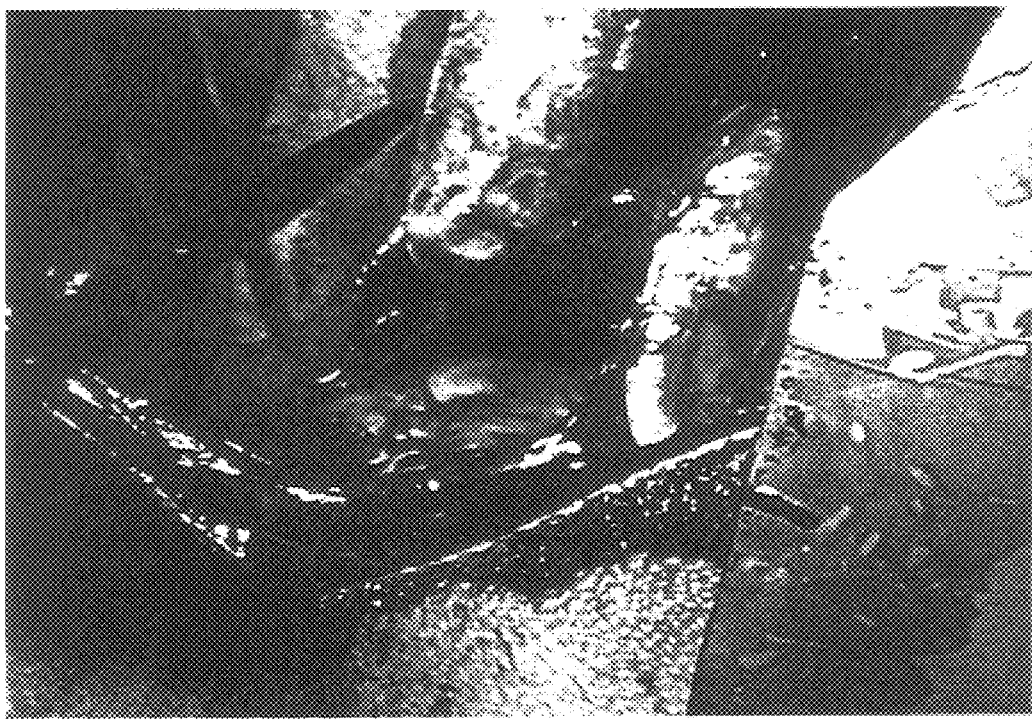
Figure 9C:
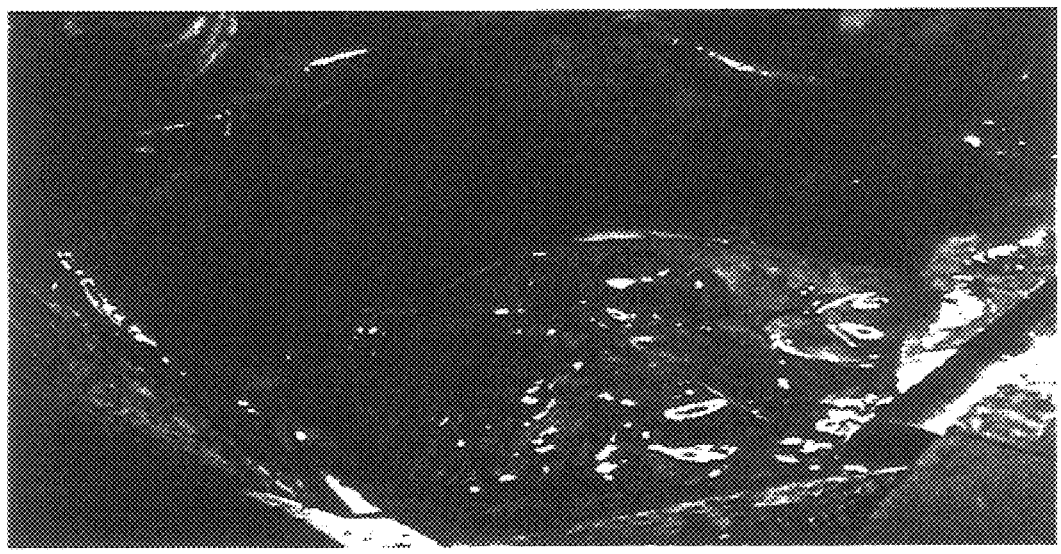
Figure 9D:
Figure 9E:
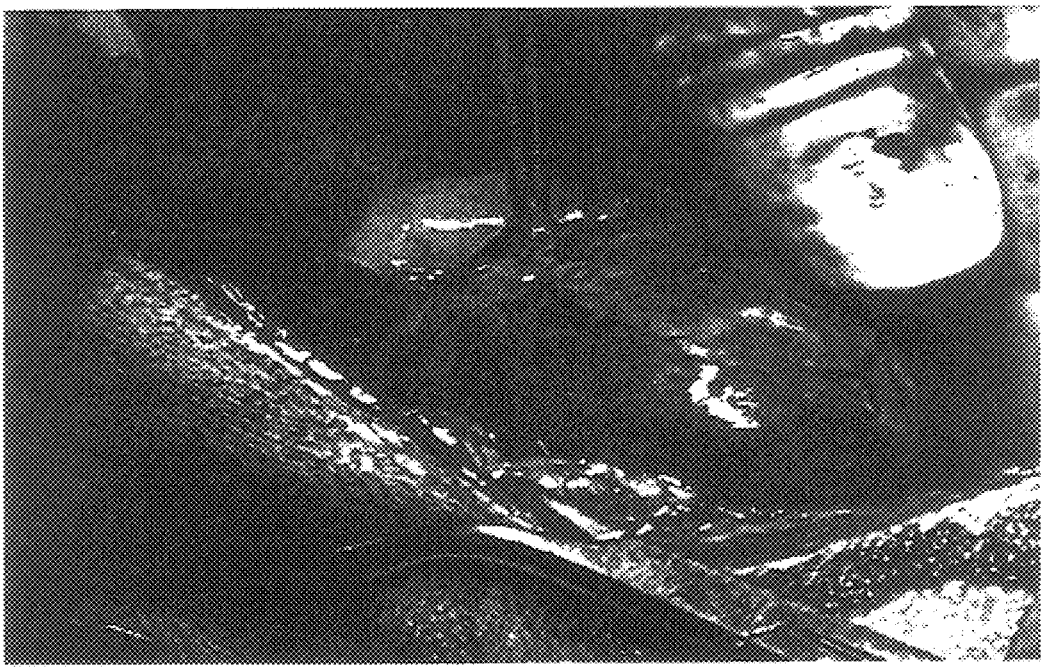

In the second series of 3 dogs, terminated at 5 and 6 months, the underside of the pericardium was abraded on either side of the phrenic nerve. Dorsal side was the control and ventral side the test area in which the Patch intervened between the epicardium and pericardium. In this series the pericardium was also not closed. In all three cases there were strong adhesions (grade 3–4) on the unprotected side (dorsal) (see FIG. 7D) and no adhesions on the protected side (ventral) (see FIG. 7B). This was true even when in one case the Patch moved and slipped from the original placement location. It was also evident from this series of experiments that the Patch was completely bio-adsorbed by 5–6 months (see FIG. 7A). In another case, weak adhesion formations (grade 0.5–1) occurred in the area not protected by the Patch (see FIG. 7C).

In the third series of experiments, 5 dogs were subjected to Left Internal Mammary Artery (LIMA) Anastomosis (see FIGS. 8A–8E and 9A–9E). This is a mimic for an actual by-pass procedure currently used on human patients. In this procedure two Patches were used in each experiment. One patch was attached to the epicardium and intervened between anastomosis and the heart and between anastomosis and the pericardium. The second patch was attached to cover the closure slit in the pericardium. Two of these dogs have so far been terminated and there was no evidence of the Patch or any adhesions. These dogs remain in the study until later.

The overall results indicate that PAP prevents adhesion. In eight in vivo experiments wherein two different procedures were utilized, 12.5% of the cases had grade 1 adhesions (which can be resolved with a single pass of the gloved finger), and the remaining 87.5% showed no adhesions at all. In all cases the coronary vasculature was visible at the beginning, in the intermediate stages of the experiment, and certainly when the Patch had been absorbed. In 16 experiments, there had been no deaths, or inflammatory or rejection reactions. Neither were there any cardiological episodes.

One of the animals was intubated for fluid withdrawal and examination. Antibodies directed against the surface antigens on canine lymphocytes or macrophages are not commercially available. Using mouse antibodies against macrophages, lymphocytes and T cells, the exhudate in the thoracic cavity was evaluated by flow cytometry. This showed that in the first week post surgery macrophages and lymphocytes were the only inflammatory cells present (T cells were absent) indicating a normal post-traumatic inflammation. With the approval of the Institutional Animal Care Committee (IAC), another dog has been implanted subcutaneously with an additional Patch three weeks before termination of the experiment. The rational is that if there is an immunogenic response to the components of the PAP, then the animal would be sensitized due to two patches used in the LIMA procedure and additional implantation would elicit a significant if not massive immune reaction. There has been no immune response in two weeks. This experiment will be repeated with the remaining two dogs in the LIMA study. Two additional animals will be treated in the same fashion.

It is believed that the three dogs remaining in the study will also show no adhesions. Therefore it is contended that the proof of principle has been demonstrated for this invention. The efficacy and safety of this method of adhesion prevention is suitable for other anatomical locations and will be subjected to further clinical evaluation.

EXAMPLE 18

Summary and Discussion

The above experiments demonstrate that Patch works best if it is attached to one of the surfaces that has been traumatized and participates in formation of the adhesion. In some locations attachment to one surface might be more important then in others. For this purpose fibrin tissue glues, other types of bio-adhesives or alternative FDA approved methods of attachment are suitable. The Nitinol Couplers are biologically inert and are based on a new FDA approved technology. They are easy to use, effective, and safe even on the sensitive surface such as epicardium. However, they may not be suitable for all anatomical locations (e.g. brain).

Although the Patch has only been evaluated in the thoracic cavity of an in vivo model, it could be utilized with equal efficiency in a number of anatomical locations provided the method of attachment for that location is also established, since its mechanism of action and dissociation is global. For example, the physical form of the Patch lends it suitable for orthoscopic and laparoscopic procedures provided the attachment to one of the traumatized surfaces can be made. Thus the Patch might be rolled into a tubular structure, without adhering to itself, and delivered through a lubricated orthoscope or laparoscope, wherein some anti-adhesion barriers (e.g. Seprafilm®) are too adhesive to be used in this type of procedure.

Additionally, the Patch disclosed in the present invention might be easily stored moist, sterile and refrigerated. It is easy to pick up the Patch and manipulate it with surgical instrument used in most procedures.

Discussion: The present approach is based on two paradigm shifts. The first of these is a departure from the established strategy of inert rapidly dissociating barriers to that producing slowly absorbed barrier that actively participate in the mechanism of prevention of adhesion formation. The second paradigm shift is that attachment of anti-adhesion barrier to the epicardium does not have to cause foreign body reaction.

The present Patch is designed to be a collagenous, but not fibrin based internal scar tissue. The density of the Patch is such that it is amenable to cell invasion and can be a scaffold for a variety of cell. For example it becomes vascularized, i.e. microvessels are observed in the Patch when the surgical site is examined early after surgery (4–8 weeks). The vascualrization assists in the biodegradation of the Patch because it makes the Patch more accessible to macrophages and lymphocytes. Since macrophages secrete collagenases, they are involved as the major player in the mechanism of biodegradation of the Patch. Both cell types support the inflammatory phase of the wound healing process and tissue remodeling which is a slow process of matrix dissolution. Since the Patch is collagenous, its dissolution is not dependent on fibrinolytic activity and the presence of secreting mesothelium. The collagenous matrix of the Patch is not adversely affected by blood. Therefore, there is no need that meticulous heamostasis be established.

Since the epicardium is not covered by the mesothelium, when the patch is attached, it adheres only to this internal surface. There have been no foreign body reactions in any of the in vivo experiments as a result of attachment of the patch to the epicardium. Furthermore because the density of the Patch allows retention of the initial translucency, the cardiac vasculature is not obscured by the Patch.

While the invention has been shown in several of its forms, it is not thus limited but is susceptible to various changes and modifications without departing from the spirit thereof.

What is claimed is:

1. A method of constructing an anti-adhesion patch, comprising the steps of:
   (a) mixing human connective tissue cells with a collagenous material;
   (b) incubating the resulting mixture in a matrix organization medium to stimulate the cells to adapt to and organize the collagenous material into a mono-cellular tissue equivalent having desirable dimensions and mechanical properties;
   (c) treating the tissue equivalent to eliminate the cells; and
   (d) confirming the absence of viable cells in the tissue equivalent after the treatment, wherein said tissue equivalent may be used as an anti-adhesion patch.

2. The method of claim 1, wherein said collagenous material is in an acid solution and first neutralized at 4° C. before the mixing step.

3. The method of claim 2, wherein said acidic solution is hydrochloric solution.

4. The method of claim 1, wherein said human connective tissue cell is a fibroblast cell or a vascular smooth muscle cell.

5. The method of claim 4, wherein said fibroblast cell is a dermal fibroblast cell.

6. The method of claim 1, wherein said collagenous material is collagen type I or a combination of collagen type I and a co-component.

7. The method of claim 6, wherein said co-component is selected from the group consisting of elastin, interstitial collagens, collagen type III, V and IX, glycoproteins and proteoglycans.

8. The method of claim 1, wherein said collagenous material is from a natural source or a recombinant source.

9. The method of claim 1, wherein said matrix organization medium contains fetal bovine serum.

10. The method of claim 1, wherein said matrix organization medium is a serum-free cocktail of growth factors selected from the group consisting of fibroblast growth factor (FGF), epidermal growth factor (EGF), platelet derived growth factor (PDGF), transforming growth factor beta ($TGF_\beta$) and a mixture thereof.

11. The method of claim 10, wherein said cocktail of growth factors are in the presence of growth promoters.

12. The method of claim 11, wherein said growth promoter includes transferrin and insulin.

13. The method of claim 1, wherein the cell-elimination treatment includes nutrient deprivation, antibiotics treatment and anti-mitotics treatment.

14. The method of claim 13, wherein said antibiotics includes puromycin, amphoteracin and mitomycin.

15. The method of claim 13, wherein said anti-mitotics is 5-flurouracil.

* * * * *